United States Patent [19]

Ullman

[11] 3,998,943
[45] Dec. 21, 1976

[54] DOUBLE RECEPTOR FLUORESCENT IMMUNOASSAY

[75] Inventor: Edwin F. Ullman, Atherton, Calif.

[73] Assignee: Syva Company, Palo Alto, Calif.

[22] Filed: Oct. 2, 1973

[21] Appl. No.: 402,693

[52] U.S. Cl. ............................. 424/12; 23/230 B; 195/103.5 R; 260/112 B; 252/301.16
[51] Int. Cl.$^2$ ................. G01N 21/00; G01N 33/16
[58] Field of Search ................... 23/230 B; 424/12; 195/103.5 R; 260/112 B; 252/301.16

[56] References Cited
UNITED STATES PATENTS

| | | | |
|---|---|---|---|
| 3,656,906 | 4/1972 | Bullock | 23/230 B |
| 3,709,868 | 1/1973 | Spector | 424/12 X |
| 3,766,162 | 10/1973 | Spector | 23/230 B X |
| 3,775,536 | 11/1973 | Spector | 23/230 B X |
| 3,789,116 | 1/1974 | Kay | 424/12 X |
| 3,809,782 | 5/1974 | Spector | 23/230 B X |
| 3,817,706 | 6/1974 | Smith | 23/230 B |
| 3,901,654 | 8/1975 | Gross | 23/230 B |
| 3,935,074 | 1/1976 | Rubenstein | 23/230 B |

OTHER PUBLICATIONS

Chemical Abstracts, 73:64436m (1970).
Chemical Abstracts, 73:48541m (1970).
Chemical Abstracts, 79:101164t (1973).

*Primary Examiner*—Morris O. Wolk
*Assistant Examiner*—Sidney Marantz
*Attorney, Agent, or Firm*—Townsend and Townsend

[57] ABSTRACT

A sensitive method for determining qualitatively and quantitatively the presence of a wide variety of physiologically active organic compounds (ligand) is provided. The method employs a reagent which involves bonding a compound having structural similarity to the compound to be determined (ligand analog) to a fluorescing compound. The unknown compound is referred to as a ligand, the conjugate of the structurally similar compound and fluorescer is referred to as ligand analog-fluorescer, and compounds which recognize a specific structure and bind to such structure are referred to as receptors and are normally antibodies.

The fluorescer which is chosen will have either a change in quantum yield or a change in its emisson and/or absorption spectra or all of them, when bound to antibody, as compared to being unbound. For the purposes of the assay, all that is required is that there be a change in the emisson intensity at some wavelength or band of wavelengths.

The rate at which fluorescer antibody binds to the fluorescer portion of the ligand anaog-fluorescer or the amount of fluorescer antibody bound to the fluorescer portion of the ligand analog-fluorescer at equilibrium will be related to the amount of ligand antibody bound to the ligand analog portion of the ligand analog-fluorescer. Therefore, by combining antibodies to both ligand and fluorescer, with ligand analog-fluorescer and an unknown, one can determine the amount of ligand present in the unknown by relating the emission intensity at a particular wavelength or band of wavelengths to standards.

17 Claims, No Drawings

DOUBLE RECEPTOR FLUORESCENT IMMUNOASSAY

BACKGROUND OF THE INVENTION

Field of the Invention

There is a continually expanding need to determine the presence of minute quantities of organic materials. Concentrations of interest range from about $10^{-4}$ to $10^{-12}$M or even lower. Areas where the determinations are significant include the presence of drugs of abuse in physiological media, the metering of therapeutic dosages of drugs, disease diagnosis, where the presence, absence or amount of a particular organic material is relevant to the diagnosis of the disease and assaying for trace components in food. Other areas which are not of physiological interest include scientific investigation and assaying for trace contaminants in water or other fluids, quality control, and the like.

One approach to assays for specific materials comes under the class of immunoassays. Immunoassays employ a receptor, normally an antibody, which recognizes a specific spatial structure and charge distribution—epitope—in an organic molecule. The antibodies are relatively large molecules, of 150,000 or greater molecular weight and are protein in nature. Therefore, with most organic compounds of interest, the binding of the antibody to the organic compound provides significant enhancement in molecular weight, as well as a change in the environment of the organic compound, as compared to the solvent environment. In immunoassays, aqueous solvents are normally employed.

In radioimmunoassay, the great enhancement in molecular weight allows for separation of an organic compound which is bound to antibody and unbound organic compound. By having a detector molecule which is radioactive, one can determine the distribution of the radioactive compound between bound and unbound. This distribution is related to the concentration of the organic compound present in the unknown.

A second technique is a spin immunoassay technique, supplied by Syva Company, under the trademark FRAT. In this technique, a stable free radical compound is bound to a compound resembling the unknown organic compound. The rate at which the spin label compound tumbles in solution affects the height of the electron spin resonance spectrum. When the spin label compound is bound to antibody, the rate is substantially slower than for the unbound compound. By relating the peak height of the electron spin resonance spectrum to known standards, one can determine the amount of the unknown compound present in the solution.

Another technique uses an enzyme as the detector. In this technique, an enzyme is bound to the unknown compound. In this technique, which is sold by Syva Company, under the trademark EMIT, when the enzyme-bound compound is bound to an antibody, there is a substantial reduction in the enzyme activity. Therefore, by metering the enzyme activity, and relating enzyme activity to a standard, one can determine the amount of unknown in a solution.

DESCRIPTION OF THE PRIOR ART

U.S. Pat. No. 3,709,868 is exemplary of a radioimmunoassay. U.S. Pat. No. 3,690,834 is exemplary of a spin immunoassay. U.S. Pat. No. 3,654,090 and German Auslegungsschrift 2,223,385 are exemplary of enzyme immunoassays. Articles of interest include an article by Ludwig Brand and James R, Gohlke, entitled, Fluorescence Probes for Structure, *Annual Review of Biochemistry*, 41, 843–868 (1972) and Stryer, *Science*, 162, 526 (1968)

SUMMARY OF THE INVENTION

A method is provided for determining the presence or amount of an organic compound to which a receptor, usually antibody, is available or can be prepared. The organic compound will be hereinafter referred to as a ligand. The reagents employed are (1) a ligand analog-fluorescer, (L.A-F.) where the ligand portion of the L.A-F. has substantially the same epitope as the ligand (2), antibody for the ligand (antiligand) and (3) antibody for the fluorescer (antifluorescer). When the reagents are combined with the unknown sample in an aqueous medium at a suitable pH, the resulting emission spectrum will be related to the amount of ligand present in the solution. This is a result of the amount of fluorescer bound to antifluorescer being related to the amount of ligand present in the unknown sample, and the difference in emission spectrum between unbound fluorescer and fluorescer bound to antibody.

BRIEF DESCRIPTION OF THE SPECIFIC EMBODIMENTS

The subject invention provides a novel and sensitive method for determining the presence of a wide variety of organic compounds for which a receptor is available or can be prepared. In practice, the invention is employed with antigens or haptens as a ligand, whose presence or concentration is to be determined. A reagent is prepared combining a compound having at least one epitope in common with the ligand (hereinafter referred to as the ligand analog) to a fluorescer. The ligand analog will normally have substantially the same spatial characteristics and charge distribution as the ligand, so as to be able to compete satisfactorily with the ligand for receptor sites, e.g. antibody sites. The epitope of the ligand analog is in sufficient proximity to the fluorescer, so that for the most part, antibody for fluorescer and antibody for ligand cannot reside similtaneously on the same molecule. When ligand analog-fluorescer is combined in solution with antibody for the fluorescer and antibody for the ligand, an equilibrium is established related to the binding constants of the two antibodies. If ligand is introduced into the solution, the equilibrium of the antibodies with the ligand analog-fluorescer is changed, since the effective concentration of antibody for ligand analog is reduced.

The emission spectrum of the fluorescer is sensitive to its environment. Therefore, the emission spectrum will change when the fluorescer is bound to an antibody as compared to when the fluorescer is unbound. The change may be caused by a change in the quantum yield or in the emission or absorption spectrum. By considering a single wavelength, comparing the relative intensity of two wavelengths, or integrating a band of wavelengths, one can determine the presence or amount of ligand present in an unknown sample by comparing the signal intensity to the signal intensity of a standard.

In order to illustrate the subject method, the following equations indicate the various reactions which occur:

1. In the absence of ligand $$L.A\text{-}F + Ab_F + Ab_L \rightleftharpoons L.A\text{-}F/Ab_F + Ab_L/L.A\text{-}F$$

$$L.A\text{-}F + h\nu \rightarrow L.A\text{-}F^* \rightarrow L.A\text{-}F + h\nu^1$$

$$Ab_L/L.A\text{-}F + h\nu \rightarrow Ab_L/L.A\text{-}F^* \rightarrow Ab_L/L.A\text{-}F + h\nu^1$$

$$L.A\text{-}F/Ab_F + h\nu \rightarrow L.A\text{-}F^*/Ab_F \rightarrow L.A\text{-}F/Ab_L + h\nu^2$$

In the presence of ligand, there is the additional reaction:

$$L + Ab_L \rightleftharpoons L/Ab_L$$

In the above equations, the various reactions and products are identified as follows:

L.A-F — ligand analog (L.A.) bonded to fluorescer (F)

X/Y — intends X bound to Y, e.g. antibody for fluorescer ($Ab_F$) bound to fluorescer (F)

$h\nu$ — photon; the one and two indicate light of different emission intensity

* — intends excited state.

If one begins with a solution having a fixed concentration of L.A.-F. fluorescer antibody (antifluorescer) and ligand antibody (antiligand), it is evident that the presence of ligand will reduce the available amount of antiligand, so as to change the equilibrium which exists in the absence of ligand. Since the emission intensity and/or wavelengths of emitted light are different for fluorescer bound to antibody as compared to unbound fluorescer, the emission spectrum will vary depending on the amount of ligand present in the solution.

In carrying out an assay, the reagents can be combined in any order. However, there are certain considerations, which make certain orders of addition highly preferable. One such consideration is that it is found that displacement is relatively slow. That is, once the ligand or ligand analog has become bound to an antibody, displacement of one by the other proceeds over a relatively long period of time. Furthermore, while both the ligand and ligand analog may be bound strongly to the antibody, the binding constant might vary substantially between the two. Therefore, if the ligand analog had a substantially higher binding constant than the ligand at equilibrium, the amount of ligand which had displaced the ligand analog might be very small. This would introduce a high degree of inaccuracy in the method.

Also, essential to the method of analysis, is that the presence of antiligand bound to ligand analog block the binding of antifluorescer to the fluorescer. Since displacement of antiligand from ligand analog by antifluorescer will be slow, and the method of determination is based on the distribution of bound and unbound fluorescer, normally, antiligand and ligand analog-fluorescer will be combined prior to the addition of antifluorescer.

In view of the above considerations, the normal mode of addition will have two major variants: combining of unknown and antiligand, followed by the addition of ligand analog-fluorescer; and combining of unknown, ligand analog-fluorescer and antiligand. When a relatively stable state after standing or incubation has been achieved, either as to a reproducible change in concentration of the various reaction species per unit time, or substantially constant concentrations of the various reaction species, the available fluorescer may then be titrated with or an excess added of antifluorescer. Usually, the minimum time period required between additions will be less than about two hours.

The value can be determined as the value obtained after a specified time duration—a rate—or a value which subsists or changes very slowly over an extended period of time. In the latter situation, a true equilibrium not normally be attained, but rather a distribution of antibody based on relative concentrations of the various species, rather than relative binding constants. For the purposes of this invention, this can be considered an equilibrium, since the value read will change only slowly with time.

By determining the emission spectrum employing a particular light source of constant intensity, and observing the emission intensity at a particular wavelength or a particular band of wavelengths, one can relate this result to known standards. By carrying out the procedure with the unknown in substantially the same manner as carried out with the standards, a qualitative or quantitative determination of the amount of ligand present in the unknown sample may be achieved.

The concentrations of ligand which may be assayed for will vary from about $10^{-4}$ to $10^{-12}$, more usually from about $10^{-5}$ to $10^{-11}$M. The concentration of ligand analog-fluorescer will also vary in the same range, usually not differing by more than a factor of 100 from the concentration range of interest. The antibody concentrations will generally be from about 0.5–1000:1 in number of binding sites per mole of ligand analog-fluorescer, more usually 1–10:1 in number of binding sites per mole of ligand analog-fluorescer. See U.S. Pat. No. 3,690,834, for a method of determining binding sites. The mole ratio employed of antibody to ligand analog and fluorescer will depend to a significant degree on the binding constant of the antibody.

As already indicated, the medium will normally be aqueous, generally having not more than about 20% by volume of a polar organic solvent. Various alcohols, ketones, ethers and esters may be present in minor amounts.

The pH of the medium will normally be in the range of about 6 to 9, more usually in the range of about 7 to 8.5. Various buffers may be used to achieve the desired pH and maintain it during the determination. Illustrative buffers include borate, phosphate, carbonate, Tris, barbital, and the like. The particular buffer employed is not critical to this invention, but in particular assays, one buffer may be preferred over another.

With certain ligands and fluorescers, there may be small but significant amounts of non-specific binding of the ligand or fluorescer to protein. To that extent, it is preferred that the protein concentration of the assay medium be less than one weight percent, preferably less than 0.5 weight percent and particularly preferred, less than about 0.1 weight percent. The total protein concentration may be minimized by prior treatment of the unknown sample by ultrafiltration, gel filtration, precipitation, dialysis, and the like.

Moderate temperatures are normally employed for carrying out the assay and usually constant temperatures during the period of the assay will be employed. The temperatures normally range from about 15° to 40° C, more usually from about 25° to 40° C. Higher temperatures are not desirable, since they reduce the binding of the antibodies to the epitopes.

In carrying out the determination, the assay solution is introduced into the fluorometer cell. The choice of excitation wavelength will depend on the fluorescer. The particular wavelength or band of wavelengths which are measured for the emission spectrum will depend on the emission maximum and the amount of interference due to light scattering. Desirably, an intense source of light of a single wavelength will be used. In this manner, interference from light scattering effects can be minimized. Useful monochromatic light sources that provide greater intensity than conventional sources coupled with a monochromator are low pressure emission lamps and lasers.

The primary reagent involved in the subject invention is the ligand analog-fluorescer molecule. This molecule must compete with the ligand for receptor sites or at least be capable of being specifically bound to receptor sites which bind to the ligand.

The binding constant of the antiligand for ligand should not be too dissimilar to the binding constant for the ligand analog. If the ligand fluoresces, the fluorescer should have an emission intensity at the measured wavelength(s) at least about 100 times greater than the ligand at the highest concentration of ligand likely to be encountered or measured. The lower fluorescence of the ligand may be as a result of a different absorption maximum from the fluorescer, a different emission maximum or a substantially lower quantum efficiency.

As indicated, the ligand will vary widely, normally having a molecular weight of at least 110, more usually at least 125 with the maximum molecular weight unlimited, although usually not exceeding 10 million. For the most part, the significant factor concerning a ligand is that a receptor can be made to the ligand or is available. Normally, receptors can be made for most organic compounds having a polar functionality. Compounds for which antibodies can be formed by bonding the compound to a compound having antigenic properties are referred to as haptens. Those compounds which elicit antibody formation without chemical modification are referred to as antigens. See Kabat, et al., Experimental Immunochemistry, Charles C. Thomas, Springfield, Illinois, 1967.

The non-polymeric compounds of interest will normally be of from about 125 to 2,000 molecular weight. These compounds involve a wide variety of compounds of varying structure, functionality, and physiological properties. The compounds may be acyclic, alicyclic or heterocyclic, both mono- and polycyclic. The heteroatoms involved include oxygen, nitrogen, sulfur, halogen (fluorine, chlorine, bromine and iodine) boron, phosphorous, metal cations of Groups 1A and 2A of the Periodic Chart and the like.

The functionalities include alcohols, ethers, carboxylic acids, esters and amides, amines (primary, secondary, tertiary and quaternary) halo, nitrilo, mercapto, and the like. Normally, the compounds will be composed solely of carbon, hydrogen, oxygen, nitrogen, halogen and phosphorous, particularly carbon, hydrogen, oxygen, and nitrogen and where salts are involved, the appropriate metal counterion or ammonium counterion.

Heterocyclic rings which are present include pyrrole, pyridine, piperidine, indole, thiazole, piperazine, pyran, coumarin, pyrimidine, purine, triazine, imidazole, and the like.

Because of the wide variety of compounds which can be determined in accordance with the subject assay, the different groups will be broken down into various, frequently artificial, categories, either by the presence of a particular functionality or ring structure, or because of sharing a particular function or because of being recognized as a class.

The first class of compounds of interest are those having an amino group, either as a heterocyclic member, or as a functionality on an aliphatic chain. These compounds will normally be of from about 110 to 800 molecular weight, more usually of about 125 to 650 molecular weight.

The first group of compounds of interest are the alkaloids and the metabolites of those alkaloids which are ingested. The first group of important alkaloids are alkaloids of the morphine group. Included in this group are morphine, codeine, heroin, morphine glucuronide and the like.

Compounds which find use in this invention as reagents for detecting morphine alkaloids and its metabolites will, for the most part, be of the following formula:

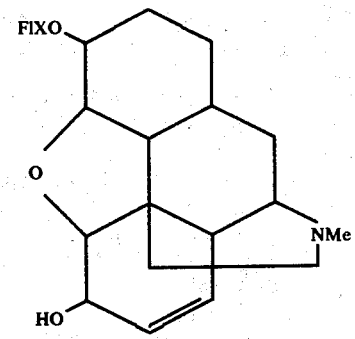

wherein X is a linking group, normally of from 2 to 8 atoms other than hydrogen, more usually of from 2 to 4 atoms other than hydrogen and being free of atoms other than carbon, hydrogen, oxygen, sulfur and nitrogen, and preferably having an non-oxocarbonyl group as part of the linking functionality. Fl is a fluorescer which will be described subsequently.

Illustrative linking groups are acetamido, acetimidino, succinate, oxalate, and the like.

The next group of alkaloids are the cocaine alkaloids, which include, particularly as metabolites, benzoyl ecgonine and ecgonine.

Another group of alkaloids are the cinchona alkaloids which include guinine.

The isoquinoline group of alkaloids includes mescaline.

The benzylisoquinoline alkaloids include papaverine.

The phthalide isoquinoline alkaloids include narcotine, narceine, and cotarnine.

The indolopyridocoline alkaloids include yohimbine and reserpine.

The ergot alkaloids include ergotamine and lysergic acid.

Other groups of alkaloids include strychnine alkaloids, pyridine alkaloids, piperidine alkaloids, pyrrolizidine alkaloids, and the like.

The alkaloids of primary interest are those which come within the category of drugs of abuse, such as morphine, cocaine, mescaline, and lysergic acid, which may be analyzed for the compound or its metabolite, depending on the physiological fluid which is analyzed for its presence.

A number of synthetic drugs mimic the physiological properties, in part or in whole, of the naturally occurring drugs of abuse. Included among these drugs are methadone, meperidine, amphetamine, methamphetamine, glutethimide, diphenylhydantoin, and drugs which come within the category of benzdiazocycloheptanes, phenothiazines and barbiturates.

Drugs of interest because of their physiological properties are those which are referred to as catecholamines. Among the catecholamines ae epinephrine, ephedrine, L-dopa, and norepinephrine.

Another drug of interest is the tranquilizer Meprobamate.

Other compounds of interest are tetrahydrocannabinol, cannabinol, and derivatives thereof, primarily compounds derived from marijuana, synthetic modifications and metabolites thereof.

Another group of compounds of significant interest are the steroids. The steroids include estrongens, gestogens, androgens, adrenocortical hormones, bile acids, cardiotonic glycoids, algycones, saponins and sapogenins.

Another class of compounds are the vitamins, such as vitamin A, the B group, e.g. vitamin $B_1$, $B_6$ and $B_{12}$, E, K, and the like.

Another class of compounds are the sugars, both the mono- and polysaccharides, particularly di- and higher order polysaccharides.

Another class of compounds is the prostaglandins.

Another class of compounds are the amino acids, polypeptides and proteins. Polypeptides usually encompass from about 2 to 100 amino acid units (usually less than about 12,000 molecular weight). Larger polypeptides are arbitrarily called proteins and are usually composed of from about 1 to 20 polypeptide chains. Poly)amino acid) will be used as generic to polypeptides and proteins. Of particular interest among amino acids is thyronines, both the tri- and tetraiodo.

Another group of compounds are the antibiotics such as penicillin, actinomycin, chloromycetin, and the like.

Individual compounds of interest are serotonin, spermine, and phenylpyruvic acid.

Finally, compounds which are pesticides, such as fungicides, insecticides, bactericides, and nematocides, may also be of interest for assaying.

In most cases, the ligand analog will replace a hydrogen of the ligand with a bond to a linking group. As for example, with morphine, the hydrogen of the phenolic hydroxyl can be replaced with a bond to the methylene of an acetyl group. The hydrogen which is replaced by a bond to a linking group may be bonded to carbon, either aliphatic or aromatic, oxygen or nitrogen.

In some instances, an oxocarbonyl may serve as the linking site by modifying the oxocarbonyl to an oxine. In other instances, the hydroxyl of a carboxyl group may be replaced to form a linking group, by forming an ester or amide.

Additional alternatives include introducing functionalities, such as hydroxyl functionalities from which ethers can be formed, amino functionalities, from which diazo groups can be formed, and the like.

The significant factor for the ligand analog is that it has sufficient structural similarity to the ligand so as to be recognized by the antibody for the ligand. Because the manner of addition can be widely varied, the binding constants for the ligand and the ligand analog may be different, but should not differ by more than a factor of $10^3$, preferably by not more than a factor of $10^2$.

For the most part, the ligand analog will have the same or substantially the same structure and charge distribution (spatial and polar organization) as the ligand for a significant, if not major, portion of the molecular volume. Since frequently the linking site for a hapten will be the same as in preparing the antigen for production of antibodies as used for linking to the fluorescer, the same portion of the ligand molecule which provides the template for the antibody will be exposed by the ligand analog when bound to fluorescer.

Because of the steric inhibition of the presence of one antibody preventing the binding of another antibody to the ligand analog-fluorescer, the linking group will normally be relatively short. Usually, the linking group will be substantially less than 25 A, more usually less than 20 A, and preferably less than 15 A. Normally, the linking group will be from about 1.5–10A.

With large molecules or macromolecules as ligands, such as polypeptides and proteins, there will be a number of different epitopes available on the surface of the molecule, each of which will have a complementary antibody. When the macromolecule is conjugated with fluorescer, normally there will be a plurality of fluorescer molecules bonded to the macromolecule. Depending on the spatial relationship of the fluorescer molecule to an epitope, there may or may not be steric inhibition to the simultaneous binding of antibody to the ligand epitope and antibody to the fluorescer. However, there will normally be a plurality of pairs of epitope sites and fluorescer molecules, where to various degrees, steric inhibition between the two different antibodies will exist. In referring to ligand analog-fluorescer molecules, it is intended to include molecules where there are a plurality of epitope-fluorescer pairs, which are in appropriate juxtaposition for steric interaction. The statement concerning the simpler molecules having one epitope and one fluorescer will be normally appropriate to the epitope-fluorescer pairs present in macromolecules.

In choosing the fluorescer, a wide variety of considerations will come into play. As already indicated, the choice of fluorescer will, to a degree, be governed by the ligand. Therefore, one consideration is that the fluorescer have absorption at higher wavelengths than a fluorescent ligand or ligand bound to antibody.

In addition to the considerations which relate to the particular ligand being determined, there will be a number of other considerations which limit the particular choice of fluorescer. As a practical matter, since one is concerned with a change in the emission spectrum as a result of being bound or unbound to an antifluorescer, one would desire a large environmental effect on the emission intensity at a particular wavelength. This can be a result of a substantial change in quantum yield or a change in the emission or absorption spectrum in going from the bound to unbound fluorescer.

Since proteins absorb at a wavelength of about 280, the fluorescer should have an absorption maximum above 300, usually above 350 and preferably above 400. The extinction coefficient should be greatly in excess of 10, preferably in excess of $10^3$, and particularly preferred, in excess of $10^4$.

In addition, it is desirable that the fluorescer have a large Stokes shift. That is, it is preferred that there be a substantial spread or difference in wavelengths for the fluorescer between its absorption maximum and emission maximum.

Another consideration where physiological fluids are concerned is non-specific binding of the fluorescer to protein. Preferred fluorescers will have minimal non-specific binding, so that the primary or sole effect seen is the binding of the fluorescer to its antibody.

A number of different fluorescers are described in the articles previously noted; namely, Stryer, supra and Brand, et al., supra.

One group of fluorescers having a number of the desirable properties described previously are the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group, and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate. The naphthalene compounds are found to have some non-specific binding to protein, so that their use requires employment in an assay media where the amount of protein is minimized.

As already indicated, the linking group may be derived from a functionality which is present on the fluorescer or a funtionality which is present on the ligand analog. Either the fluorescer or ligand analog may be modified in order to provide the necessary linkage between the two compounds.

The following examples are by way of illustration and not by way of limitation.

EXPERIMENTAL (All temperatures not otherwise indicted are in centigrade).

I. Preparation of dansyl-BSA (bovine serum albumin) conjugate

Into a scintillation vial was placed 10.0 mls of 0.1M $PO_4$ buffer, pH 7.0 and 500mg BSA ($7.8 \times 10^{-6}$M) (Miles Labs.). Then, 100mg 1-dimethylaminonaphthyl-5-sulfuryl chloride (DANSC) ($3.7 \times 10^{-4}$ Moles) (Seikagaku Kogyo Ko. Ltd., Japan) was added in 1ml acetone, and the mixture was stoppered, covered with aluminum foil, and placed in the center hole of a vortex mixer and shaken at low speed overnight. The following morning, excess DANSC was removed by filtration through a plug of cotton. The filtrate was applied to a 5 × 70cm column of Sephadex G-25 and eluted with 0.1M $PO_4$, pH 7.0, flow rate 50 mls/hr, collecting 9ml fractions. Fractions 57-76 were pooled (yellow-orange in color) and concentrated by ultrafiltration through Dow hollow fibers. The concentrated solution had a protein content of 4 mgs/ml. This solution was adjusted to 0.15M NaCl and filtered through 0.25μ Millipore filters to sterilize. Samples of 2ml volume were put into sterile vials for making up injections.

Ultraviolet analysis of the dansyl-BSA conjugate confirmed the presence of dansyl on BSA by its absorption at 340 mμ. By utilizing the experimentally determined value of ε for dansyl on protein of $3.3 \times 10^3$ the hapten number for this conjugate is 13.5 dansyl/BSA.

The fluorescence properties of this conjugate were examined briefly. The parameters were: excitation maximum at 338 mμ, emission maximum at 498 mμ.

II. Preparation of insulin-dansyl conjugate

Into a scintillation vial containing 3ml of saturated $NaHCO_3$ was placed 16.7mg ($2.9 \times 10^{-6}$ Moles) of porcine insulin. To this solution was added 9.6mg ($3.6 \times 10^{-5}$ Moles) of DANSC dissolved in 1ml of dioxane. A yellow precipitate appeared immediately which dissolved upon addition of 0.5ml dioxane. To clear up a very faint white precipitate (carbonate) 0.5ml $H_2O$ was added. This solution was then capped and covered with aluminum foil, placed in the center hole of a vortex mixer and shaken gently overnight. The next morning the solution was acidified to pH 5 with acetic acid, then applied to a 2.5 × 30cm column of Sephadex G-10 and eluted with 0.2M HOAc, flow rate 10 ml/hr. Fraction volume was 1.6ml. Four peaks were observed. The first peak (Fractions 17-22) exhibited fluorescence emission and excitation spectra typical of dansyl-protein conjugates.

III. Preparation of fluorescein-BSA conjugate

Into a scintillation vial was placed 180mgs of BSA ($2.6 \times 10^{-6}$ Moles) (Pentex, crystallized) dissolved in 6mls $H_2O$ containing 180mgs $K_2CO_3$. To this was added 18.3mgs fluorescein isothiocyanate (FITC) ($4.85 \times 10^{-5}$ Moles) and the mixture was stoppered, covered with aluminum foil then placed in the center hole of a vortex mixer and shaken gently overnight at room temperature. The following morning the reaction mixture was acidified to pH 4 with 1N HCl (heavy preciptate), then made basic to pH 8 with 0.1N NaOH, applied to a 2.5 × 30cm column of Sephadex G-10 and eluted with 0.05M $PO_4$, pH 8.0 at 5.4 mls/hr, 0.9 ml/fraction. Fractions 43–72 were pooled. Hapten number was calculated from the UV absorption of the conjugate at 493mμ and the extinction coefficient for protein-bound fluorescein of $7.2 \times 10^4$. Hapten number was thus calculated to be 14.5.

IV. Preparation of insulin-fluorescein conjugate

Into a scintillation vial was placed 35.1mgs porcine insulin ($6.1 \times 10^{-6}$ Moles) dissolved in 3.5mls of 0.1M $CO_3$ buffer, pH 9.2, 0.15M NaCl. To this solution was added 4.8mg FITC ($1.2 \times 10^{-5}$ Moles) and the vial stoppered, covered with aluminum foil and placed in the center hole of a vortex mixer for gentle shaking overnight. The following morning the mixture was acidified to pH 3 with 1N HCl (bubbling) resulting in precipitation of fluorescein thiocarbamyl insulin then made basic once more with 1N NaOH just until all the precipitate was in solution. This orange solution was applied to a 2.5 × 35cm column of Sephadex G-10 and eluted with 0.05M $PO_4$, pH 7.4, 0.15M NaCl. Elution rate was 12 ml/hr, 2ml fractions. Fractions 24-33 were highly fluorescent and were pooled. These fractions were applied directly to a 2.5 × 30cm column of DEAE Sephadex A-25 which had been pre-equilibrated with 0.5M Tris, pH 7.1, 7M urea, 0.1M NaCl. After application, elution was 12 mls/hr, 2 mls/fraction, with a linear sodium chloride gradient from 0.1M to 1.0M over 500mls. Salt concentration was maintained at 1.0M until the final (4th) peak was completely eluted, with monitoring at 280 mμ. The first peak was column washings, the second, unreacted insulin, then mono-, di-, tri-fluorescein insulin in that order. Purity was assessed by electrophoresis on CAM, Tris-barbital buffer, pH 8.8. Current was continued for 50 minutes, 125v, and staining was with Ponceau S. All spots were fluorescent.

V. Preparation of morphine-fluorescein conjugate

Into a reaction vessel was introduced 68.8mg (0.2mmol) $O^3$-carboxymethylmorphine in 2ml DMF, the mixture cooled to $-5°$ C and 26$\mu$l (0.2mmol) isobutyl chloroformate added. The mixture was then stirred for 45 minutes. The resulting solution was then added slowly in 0.05ml portions to 36mg 4-aminofluorescein hydrochloride (Sigma isomer II.HCl) in 1ml butanol cooled in an ice bath. The mixture was allowed to stand 90 min. before workup.

in Immunology and Immunochemistry, Vol. 1, Academic Press, New York, 1967.

The reagents which were employed were as follows: FLUMO (fluorescein-morphine conjugate, Example V) was $3 \times 10^{-6}$M in water; antifluorescein was $5.6 \times 10^{-6}$M in binding sites, in water, 0.05M phosphate, pH 8.0; antimorphine was $2 \times 10^{-4}$M in binding sites, 0.05M tris-HCl, pH 8.0, in saline solution; buffer was Tris/saline 0.05M/l, pH 8.0. Opiate solutions had 1,000 $\mu$g/ml per ml of codeine. The solution was then diluted to a final concentration of 4 mls with buffer.

All of the determinations were made at a sensitivity setting on the instrument of 4. The solutions were mixed in order from left to right as set forth in the table. Excitation light was 460nm and the emitted light read was at 516nm, with a band width of 10nm.

The following table indicates the results.

TABLE I

| Cell No | Fluorescein-Morphine Vol. $\mu$l | Anti-Fluorescein Vol. $\mu$l | Anti-Morphine Vol. $\mu$l | Codeine Vol. $\mu$l | Signal Intensity | Reading Time min. |
|---|---|---|---|---|---|---|
| 2 | 5 | — | — | — | 62 | |
| 2 | 5 | 5 | — | — | 21 | |
| 2 | 5 | 5 | 5 | — | 25 | |
| | | | | | 26.5 | 5 |
| | | | | | 27.5 | 90 |
| 4 | — | — | — | — | 8 | |
| 4 | — | 5 | — | — | 3.5 | |
| 4 | — | 5 | 5 | — | 3.5 | |
| | | | | | 5 | 5 |
| | | | | | 5.5 | 90 |
| 3 | — | — | — | — | 1.5 | |
| 3 | 5 | — | — | — | 46 | |
| 3 | 5 | — | 5 | — | 35.5 | |
| | | | | | 35 | 5 |
| 3 | 5 | 5 | 5 | — | 23 | |
| | | | | | 22.5 | 5 |
| 3 | 5 | 5 | 5 | 5 | 20 | |
| | | | | | 16 | 90 |
| 1 | — | — | — | — | 11 | |
| 1 | — | — | 5 | — | 14.5 | |
| 1 | | | | | 14.5 | 5 |
| 1 | — | 5 | 5 | — | 5 | |
| 1 | — | 5 | 5 | 5 | 5.5 | |
| | | | | | 6 | 90 |

The reaction mixture was streaked directly on a preparative thin layer chromatograph and eluted with CHCl$_3$; MeOH; HOAc (75:50:10). After repeating the chromatography, the product was extracted from the silicon gel with methanolic sodium hydroxide. The methanol was evaporated, water added, and the resulting precipitate was rinsed thoroughly. The product was redissolved in methanolic sodium hydroxide, water added, the methanol evaporated and the pH adjusted to 8.0 with HCl to provide a solution of the desired product.

In order to establish the utility of the subject compounds, the following assays were carried out. It was found that various instrument cells gave different results, so that absolute values could only be compared where the same cell was employed. The fluorometer employed was a Perkin-Elmer MPF-2a. Antibodies to the fluorescers had been prepared according to normal procedures. The bovine serum albumin conjugates were injected into sheep, and after appropriate periods of time, the antibodies harvested according to conventional techniques. For typical methods of obtaining antibodies, see Microbiology, Hober Medical Division, Harper and Rowe, 1969; Landsteiner, Specificity of Seriological Reactions, Dover Publications, New York, 1962; Kabat, et al., supra; and Williams, et al., Methods Where a reading is given but the absence of any material is indicated, only buffer was present in the cell. The reading times indicate the interval of time from the time of the first reading to the reading for the result which is reported, the first reading being made within as short an interval as possible of the mixing.

The results show that in the absence of any competition between codeine and fluorescein-morphine, the readings are relatively stable. Cell No. 2 changes 2.5 units in signal intensity over a period of 90 minutes, 1.5 units of the change having occurred in the first 5 minutes. The results in cell No. 4 demonstrate that with only the antibodies, the major change in the reading occurs in the first 5 minutes, a change of only 0.5 units occurring over a period of 85 minutes. The results in cell No. 1 show substantial stability in the readings where codeine is added to a mixture of the two antibodies. There is only a change of 0.5 units over a period of 90 minutes. Finally, the results in cell No. 3 show that with both antibodies in the presence of codeine and fluorescein-morphine, a change of 6.5 units in signal intensity is achieved over a period of 90 minutes.

Therefore, a detectable change in fluorescence is obtained when codeine is introduced into a mixture of the fluorescein-morphine and antibodies to both fluorescein and morphine.

Further studies were made with the insulin-fluorescein conjugate as prepared in Example IV.

It was found with the insulin that only the monosubstituted insulin was immunologically active. Therefore, only it was employed in the assay. The fluorescein-insulin was employed at a concentration of $1 \times 10^{-10}$M in 0.05M $PO_4$, pH 8.0. The anti-insulin solution employed was $1 \times 0$ $10^{-10}$M in binding sites (Miles Lab.). Insulin was allowed to equilibrate at $10^{-9}$M over two days in plastic and then used in an amount to provide the desired concentration at the final dilution. The insulin was employed in 0.1M $CO_3$ in saline. Fluorescein-insulin was made up in a $2 \times 10^{-10}$M stock solution and allowed to equilibrate for two days in 0.05M $PO_4$, pH 8.0. The fluorescein-insulin, insulin and anti-insulin were combined, diluted with water, and then incubated for 1 hour. At the end of this time, 120$\mu$l of anti-fluoroscein was added at a concentration of $5.6 \times 10^{-8}$M in binding sites in 0.05M $PO_4$, pH 8.0. The order of addition of the reagents is from left to right in the table. Incubation was at room temperature. The results were repeated, whereby the order of addition was changed so that insulin and anti-insulin could incubate for 1 hour at 37° C, prior to addition of fluorescein-insulin ad a second incubation for one hour at room temperature. The results were substantially the same. The same fluorometer settings were employed as previously indicated. The following table indicates the amounts of the various materials and the variation of the emission spectrum.

TABLE II

| Fluorescein Insulin ml | Insulin ml | Anti-Insulin $\mu$l | $H_2O$ ml | Insulin final conc. M, x $10^{-10}$ | Decrease in fluorescence |
|---|---|---|---|---|---|
| 2.0 | — | 10 | 2.0 | — | 0 |
| 2.0 | 0.4 | 10 | 1.6 | 1 | 16 |
| 2.0 | 2.0 | 10 | — | 5 | 21 |

The above table shows that by increasing the amount of insulin present, a decrease in the fluorescence is observed.

It is evident from the prior results that an extremely sensitive assay is provided whereby small volumes of very low concentration of ligands can be assayed for the presence of a ligand. By appropriate choice of the fluorescer, high sensitivity and accuracy may be achieved. The method is susceptible for assaying for widely differing types of ligands, such as small drug molecules having molecular weights in the range of about 100 to 1,000, polypeptides varying in molecular weight from about 500 up to many orders of magnitude greater, as well as other organic compounds. Techniques which have previously been employed for other immunoassays are useful for the present assay, such as the method of formation of the antibodies, the conjugation of the ligands to the fluorescer, and the various parameters in optimizing the binding of the antibody to the ligand and fluorescer.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of a ligand in a sample comprising:
    combining in a aqueous medium said sample;
    1. ligand analog-fluorescer, wherein said ligand analog has at least one common epitope with said ligand so as to be specifically recognizable by a common antibody, and the ligand analog and fluorescer are linked sufficiently close by a linking group, so that the simultaneous binding of antibody to ligand and antibody to fluorescer is sterically inhibited;
    2. antiligand and (3) antifluorescer;
    determining at at least one wavelength the intensity of the fluorescence from said medium related to the emission of said fluorescer or said fluorescer bond to (3) said antifluorescer, as compared to a standard having a known amount of ligand.

2. A method according to claim 1, wherein the pH of said aqueous medium is in the range of 6 to 9, the concentration of (1) ligand analog-fluorescer is in the range of $10^{-4}$ to $10^{-12}$M, and the temperature of said medium is in the range of about 15° to 40° C.

3. A method according to claim 2, wherein said concentration of (1) ligand analog-fluorescer is in the range of $10^{-6}$ to $10^{-11}$M and said pH is in the range of 7 to 8.5.

4. A method according to claim 1, wherein said ligand is of a molecular weight in the range of 110 to 2,000.

5. A method according to claim 4, wherein the concentration of (1) said ligand analog-fluorescer is in the range of $10^{-4}$ to $10^{-12}$M, the pH of said aqueous medium is in the range of 6 to 9, and the temperature of said aqueous medium is in the range of 15° to 40° C.

6. A method according to claim 5 wherein said ligand is an alkaloid.

7. A method according to claim 5, wherein said ligand is a steroid.

8. A method according to claim 5, wherein said ligand is a synthetic drug.

9. A method according to claim 5, wherein said ligand is an opiate.

10. A method according to claim 5, wherein said ligand is a mono- or poly(amino acid).

11. A method according to claim 10 wherein said ligand is insulin.

12. A method for detecting the presence of a ligand in a sample comprising:
    combining in an aqueous medium at a pH of 6 to 9 said sample, (2) antiligand, and
    (1) ligand analog-fluorescer at a concentration in the range of $10^{-4}$ to $10^{-12}$M, wherein said ligand analog has at least one common epitope with said ligand, so as to be specifically recognizable by a common antibody, and the ligand analog and fluorescer are linked together at an average distance of less than 25 A, so that the simultaneous binding of (2) antibody to ligand and (3) antibody to fluorescer is sterically inhibited,
    adding (3) antifluorescer to said aqueous medium; and
    determining at at least one wavelength the intensity of the fluorescence from said medium related to the emission of said fluorescer or said fluorescer bound to said (3) antifluorescer, as compared to a standard having a known amount of ligand.

13. A method according to claim 12, wherein said ligand is selected from a group consisting of alkaloids, steroids, amino acids, poly(amino acids), synthetic drugs, cannabinolic compounds and catecholamines.

14. A method according to claim 13, wherein said ligand analog is at a distance of not more than about 10 A from said fluorescer, and said fluorescer is selected from the group consisting of fluoresceins, rosamines and rhodamines.

15. A method for detecting the presence of a ligand in a sample comprising:
   combining in an aqueous medium at a pH of 6 to 9 said sample, and (2) antiligand:
   adding to the medium (1) ligand analog-fluorescer, wherein said ligand analog has at least one common epitope with said ligand, so as to be specifically recognizable by a common antibody, said fluorescer has an absorption maximum at a higher wavelength than said ligand analog, and said ligand analog and fluorescer are linked sufficiently close by a linking group, so that the simultaneous binding of (2) antibody to ligand and (3) antibody to fluorescer is sterically inhibited;
   following the addition of (1) ligand analog-fluorescer with (3) antifluorescer; and
   determining at at least one wavelength the intensity of the fluorescence from said medium related to the emission spectrum of said fluorescer or said fluorescer bound to said (3) antifluorescer, as compared to a standard having a known amount of ligand.

16. A method according to claim 15, wherein said ligand is selected from the group consisting of alkaloids, steroids, amino acids, poly(amino acids), synthetic drugs, cannabinolic compounds and catecholamines.

17. A method according to claim 16, wherein said ligand analog and fluorescer are linked together at a distance not greater than 10 A and said fluorescer is selected from the group consisting of fluoresceins, rhodamines and rosamines.

* * * * *